(12) United States Patent
Ender

(10) Patent No.: US 6,663,585 B1
(45) Date of Patent: Dec. 16, 2003

(54) METHOD AND DEVICE FOR MONITORING VESSEL ACCESS DURING EXTRACORPOREAL BLOOD TREATMENT

(75) Inventor: Helmuth Ender, Zeil (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 09/508,069

(22) PCT Filed: Sep. 3, 1998

(86) PCT No.: PCT/EP98/05599

§ 371 (c)(1),
(2), (4) Date: May 25, 2000

(87) PCT Pub. No.: WO99/12588

PCT Pub. Date: Mar. 18, 1999

(30) Foreign Application Priority Data

Sep. 6, 1997 (DE) .......................................... 197 39 099

(51) Int. Cl.⁷ ............................ A01M 37/00; C02F 1/44
(52) U.S. Cl. .................... 604/6.08; 604/5.01; 604/6.06; 210/645
(58) Field of Search .................................. 210/646, 103, 210/85, 87; 604/5.01, 5.04, 6.01, 6.09, 67, 6.08; 73/861.08

(56) References Cited

U.S. PATENT DOCUMENTS

| | | | | |
|---|---|---|---|---|
| 4,495,067 A | * | 1/1985 | Klein et al. | 210/257.2 |
| 5,510,717 A | * | 4/1996 | Buffaloe et al. | 210/646 |
| 5,644,240 A | * | 7/1997 | Brugger | 324/439 |
| 5,657,000 A | * | 8/1997 | Ellingboe | 128/DIG. 12 |
| 5,685,989 A | * | 11/1997 | Krivitski et al. | 210/103 |
| 5,928,180 A | * | 7/1999 | Krivitski et al. | 210/646 |

* cited by examiner

Primary Examiner—Angela D. Sykes
Assistant Examiner—Leslie Deak
(74) Attorney, Agent, or Firm—Kenyon & Kenyon

(57) ABSTRACT

A method and device for monitoring vascular access is described. A field coil is placed at a location on an extra-corporeal circulation loop connected to the vascular system of a patient, and an induction coil is placed at another different location. A voltage is supplied to the field coil, inducing an electric current in the blood. The current induces a voltage in the induction coil. Monitoring the voltage in the induction coil reveals if vascular access is defective.

11 Claims, 1 Drawing Sheet

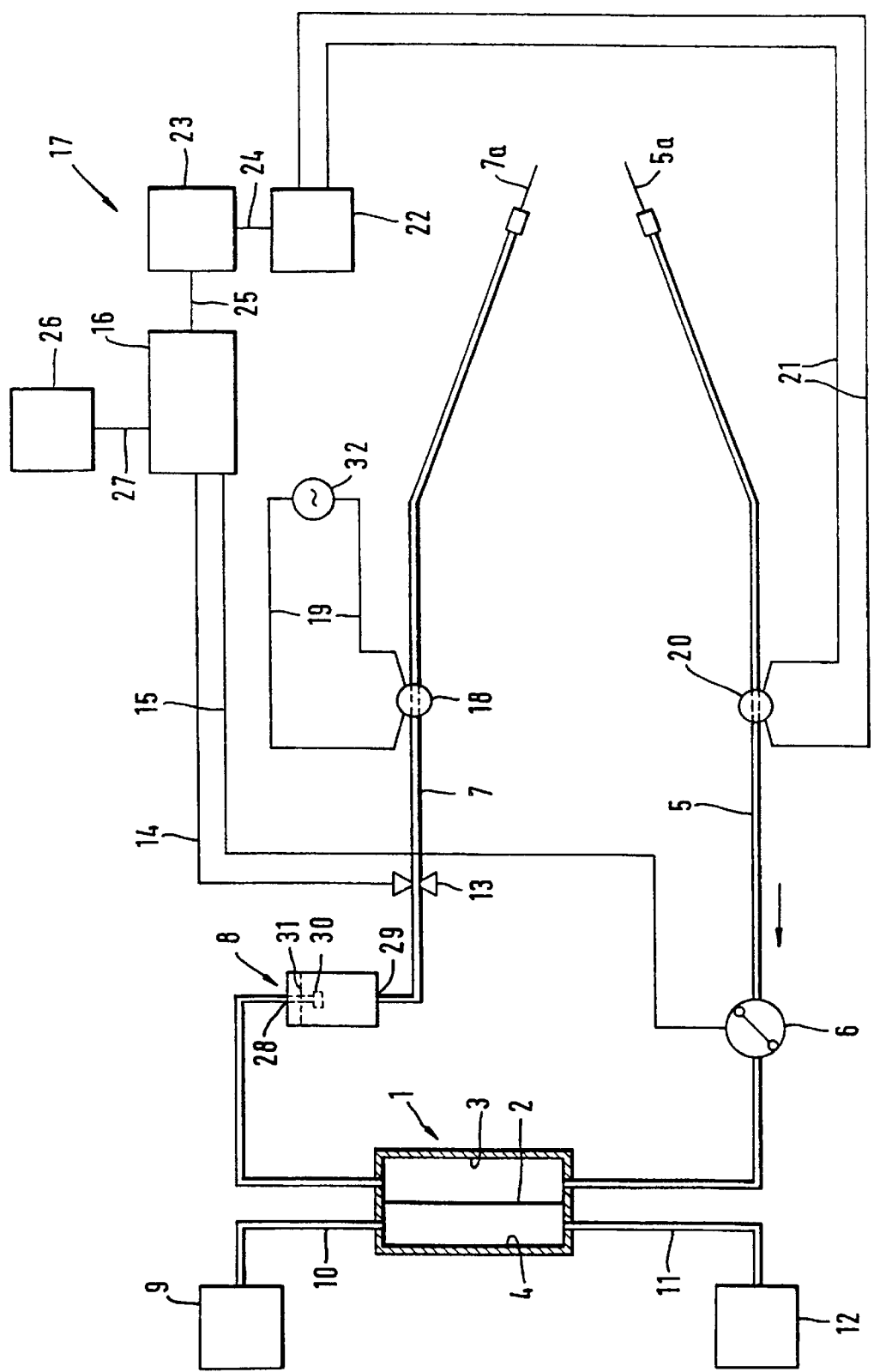

METHOD AND DEVICE FOR MONITORING VESSEL ACCESS DURING EXTRACORPOREAL BLOOD TREATMENT

The present invention relates to a method of monitoring vascular access during an extracorporeal blood treatment, in particular a dialysis or a blood separation treatment, and also relates to a device for extracorporeal blood treatment, in particular a dialysis or blood separation treatment, used for monitoring a vascular access.

DESCRIPTION OF RELATED ART

To remove substances that are normally eliminated in the urine, the blood of a kidney disease patient is passed through a chamber of a dialyzer which is subdivided by a semipermeable membrane into two chambers in an extracorporeal blood circulation system. Dialysis fluid flows through the other chamber. An arteriovenous fistula is often created for access to the vascular system, but an implant may also be used. Blood is taken from the patient through an arterial needle connected to the arterial blood line of the extracorporeal blood circulation loop, and then it is supplied back to the patient again through a venous needle connected to the venous blood line.

Cell separators, where a donor's blood is subjected to density centrifugation in an extracorporeal circulation and thereby separated into its constituents, are used to extract blood components needed for treating patients who have certain diseases.

For the safety of the patient during an extracorporeal blood treatment such as dialysis or a blood separation treatment, it is extremely important for the vascular access to be monitored. For example, if the venous needle slips out, the patient may suffer a major blood loss if this condition is not detected immediately.

Safety systems for monitoring a vascular access are known from the field of infusion technology. European Patent Application 328,162 A describes an infusion device having a pressure transducer in the infusion line for detecting the patient's heart rate as long as the needle has access to the vascular system. A defective vascular access is detected by the fact that the heart rate is no longer measured as pressure pulses in the infusion line.

European Patent Application 328 163 A describes an infusion device where the pressure pulses generated by the infusion pump in the infusion line are monitored. If a needle slips out, it is detected by a change in the shape of the pressure pulses.

Such safety systems are also used in dialysis machines. A known dialysis machine having a device for monitoring the vascular access has a pressure transducer arranged in the venous blood line. The pressure transducer detects a pressure drop that occurs when a needle slips out. However, a study of venous pressure monitoring with dialysis machines has shown the possibility of failure of a safety system based on monitoring the venous return pressure, when used to detect blood loss into the environment if a needle slips out.

International Patent WO97/10013 describes a dialysis machine having a monitoring system where pressure pulses generated by the blood pump in the arterial blood line are monitored in the venous blood line.

European Patent Application 745 400 A describes a device for monitoring the occlusive position of a peristaltic pump into which is inserted a length of tubing. With the known device, a conductor loop is created by a shunt. The shunt is an electric connection between the section of the length of tubing upstream from the pump rolls and the section downstream from the pump rolls. To monitor the occlusive position, an electric current is induced in the conductor loop with a field coil arranged upstream from the pump rolls on the length of tubing and is monitored with an induction coil arranged downstream from the pump roll. The occlusive position of the peristaltic pump is deduced from the amperage of the current flowing in the conductor loop.

SUMMARY OF THE INVENTION

The object of the present invention is to create a method of monitoring vascular access during an extracorporeal blood treatment in such a way as to permit detection of a defective vascular access with a high reliability, without requiring extensive modifications in the blood treatment equipment.

Another object of the present invention is to create a device for extracorporeal blood treatment that can detect a defective vascular access with a high reliability, and can be implemented with relatively simple technical means.

In one aspect, the invention is a method of monitoring a vascular access during an extracorporeal blood treatment, comprising the steps of flowing blood taken from a patient's vascular system through an arterial blood line of an extracorporeal blood circulation loop into a blood treatment machine, flowing blood out of the blood treatment machine back into the patient's vascular system through a venous blood line of the extracorporeal blood circulation loop thus forming a conductor loop, inducing an electric current flow in a connection of the extracorporeal blood circulation loop with the patient's vascular system, measuring a current flowing in the conductor; and determining the vascular access is defective when a characteristic change in the electric current is detected.

In another aspect, the invention is a device for extracorporeal blood treatment with an extracorporeal circulation loop, having a blood treatment machine, an arterial blood line connectable at one end to a patient's vascular system and at another end to an inlet of the blood treatment machine, and a venous blood line connectable at one end to an outlet of the blood treatment machine and at the other end to the vascular system of the patient, and a device for monitoring vascular access. The device for monitoring vascular access comprises means for inducing an electric current flow in a connection of the extracorporeal circulation loop with the patient's vascular system disposed at a first location, means for measuring the induced electric current disposed at a second location in the extracorporeal circulation loop, said second location being different the first location, and an analyzer unit to determine if the vascular access is defective by monitoring a characteristic change in the induced electric current. The blood treatment machine, the arterial blood line, the venous blood line and the patient's vascular system form a closed conductor loop.

It has surprisingly been found that the extracorporeal blood circulation, which includes the arterial vascular access, the arterial blood line, the blood treatment device, the venous blood line, the venous vascular access and the connecting vascular system of the patient or donor, forms a closed conductor loop in which an electric current can flow. Measurements have shown that the circuit is not interrupted to a sufficient extent by the blood pump connected to the extracorporeal circuit, which may also be designed as an occluding roller pump, nor by a drip chamber connected to the venous blood line.

With the method and the device according to the present invention, an electric current flow is induced in the closed conductor loop, with the current flowing in the conductor loop being measured and a defective vascular access being deduced when there is a characteristic change in amperage. A faulty vascular access is found when the circuit is interrupted, i.e. when the venous or arterial needle of the blood line has slipped out.

The impedance can be preferably measured with an alternating current whose amplitude and frequency are selected so that there can be no risk to the patient or donor, nor any damage to the blood, while on the other hand permitting signal analysis with a high reliability.

The method and device according to the present invention for monitoring a vascular access, can be used to advantage with all blood treatment methods using an extracorporeal blood circulation. These include, for example, dialysis methods or methods for separating blood into individual blood constituents. A blood treatment device as a component of a device for treating blood is understood to include, for example, a dialyzer, a filter or a separation unit of a cell separator.

To avoid intervention into the existing tubing system of a blood treatment device, the current can be expediently input into the conductor loop by inductance. In principle, however, electric contacts may also be integrated into the blood lines.

Inductive input can be preferably accomplished, for example, by using a field coil through which an alternating current flows and which is arranged at a first location in the extracorporeal blood circulation loop. An inductive output of the measurement signals can be accomplished with an induction coil which is arranged, for example, at a second location in the extracorporeal blood circulation loop. An essentially time-variable magnetic field integrated over the area enclosed by the conductor loop can be used for induction of an electromotive force along the conductor loop.

The field coils and induction coils may be arranged at any location in the extracorporeal blood circulation, but it is important for the induction coil not to be located in a leakage field of the field coil. The field coil and the induction coil can be preferably arranged on the arterial and venous blood lines, respectively.

For the case when a defective vascular access is detected, an alarm can be preferably triggered. In addition, blood flow in the extracorporeal circulation may be interrupted to prevent blood loss. Blood flow can be interrupted, for example, with a cutoff element such as a hose clamp arranged in the extracorporeal circulation.

The method according to the present invention may also be combined with other methods for detecting a defective vascular access, e.g., monitoring a pressure drop in the extracorporeal circulation. This further increases the reliability of the monitoring system.

With the method and the device according to the present invention, it is not only possible to monitor a vascular access, but it is also possible to simultaneously monitor the cutoff clamp arranged in the venous line of the known blood treatment devices.

BRIEF DESCRIPTION OF THE DRAWINGS

One embodiment of the present invention is described in greater detail below, with reference to the drawing.

The drawing shows a simplified schematic diagram of a dialysis machine having a device for monitoring a vascular access.

DETAILED DESCRIPTION OF THE EMBODIMENT OF THE INVENTION

The dialysis machine shown in the drawing has as the blood treatment device a dialyzer 1, which is subdivided by a semipermeable membrane 2 into a blood chamber 3 and a dialysis fluid chamber 4. An arterial blood line 5 is connected to the inlet of the blood chamber and to a peristaltic blood pump 6. Downstream from blood chamber 3, a venous blood line 7 leads from the outlet of the blood chamber to the patient. An air bubble separating device 8 is connected to venous blood line 7. Needles 5a, 7a which are inserted into the patient are connected to the ends of arterial and venous blood lines 5, 7. The arterial and venous blood lines can be part of a tubing system designed as a disposable pack.

Fresh dialysis fluid is prepared in a dialysis fluid source 9. A dialysis fluid supply line 10 leads from dialysis fluid source 9 to the inlet of dialysis fluid chamber 4 of dialyzer 1, while a dialysis fluid outlet line 11 leads from the outlet of dialysis fluid chamber to a drain 12.

The dialysis machine may also have other components such as a balancing device, which are not shown here for the sake of clarity.

A cutoff clamp 13 which, for example, is operated electromagnetically, can be provided on venous blood line 7 downstream from air bubble separating device 8, in order to interrupt the blood flow. Arterial blood pump 6 and venous cutoff clamp 13 are controlled by control unit 16 over control lines 14, 15.

Device 17 for monitoring a vascular access includes a field coil 18 connected by electric connecting lines 19 to an alternating voltage generator 32. Field coil 18 can be arranged at a position in venous blood line 7 downstream from hose clamps 13 so that its magnetic field permeates the area enclosed by the conductor loop. Field coil 18 is preferably a cylindrical coil whose longitudinal axis is perpendicular to the conductor loop surface. Either venous blood line 7 may pass through the field coil, or the field coil may be arranged next to the blood line, in which case the longitudinal axis of the field coil preferably forms a right angle with the blood line. Monitoring device 17 can also include an induction coil arranged at a location upstream from blood pump 6 on arterial blood line 5. Induction coil 20 is connected to a measurement amplifier 22 by electric connecting lines 21. Induction coil 20 is also a cylindrical coil whose longitudinal axis is perpendicular to the conductor loop surface, either with the arterial blood line running through induction coil 20 or with induction coil 20 being arranged next to arterial blood line 5.

Field coil 18 induces an alternating current in the extracorporeal blood circulation, its amperage depending on the conductivity of the blood, the cross section of the tubing, and other parameters. The patient's blood flows in a closed circuit that forms an electric conductor loop, through arterial blood line 5 with the length of tubing inserted into blood pump 6, blood chamber 3 of dialyzer 1, air bubble separating device 8 and venous blood line 7 as well as the vascular system of the patient. The alternating current flowing in the conductor loop in turn generates a magnetic field that is variable over time and induces a voltage in induction coil 20 on the arterial blood line, the level of this voltage depending on the amperage of the current flowing in the conductor loop. If one of two needles 5a, 7a of arterial and venous blood lines 5, 7 slips out, the circuit is interrupted, and no voltage is induced in induction coil 20.

To monitor the vascular access, the output signal of measurement amplifier 22 is compared with a predetermined reference voltage in a comparator 23 which is connected by a signal line 24 to the output of measurement amplifier 22. If the output signal of measurement amplifier 22 drops below the reference voltage, comparator 23 generates a control signal which is received by control unit 16 over a signal line 25.

Control unit 16 then switches blood pump 6 off and activates cutoff clamp 13 in venous blood line 7 to prevent blood loss. Furthermore, control unit 16 can generate an alarm signal which is received by an alarm generator 26 over a signal line 27 so that an acoustic and/or optical alarm is triggered.

To create a closed conductor loop, air bubble separating device 8 is preferably designed so that blood flows through it continuously. Such an air bubble separating device is described, for example, in German Patent 195 06 506 Al, which is herein incorporated by reference in its entirety. The device for separating blood can have, for example, an essentially round cylindrical chamber with inlet 28 and outlet connection 29 arranged in the longitudinal direction of the chamber. A flow control component 30 having a central flow tube running in the longitudinal direction of the chamber can be attached to the inlet connection 28, said flow tube developing into two flow control tubes. The circuit is not interrupted by the air bubble separating device, because the current conducting component is below liquid level 31 in the chamber.

What is claimed is:

1. A method of monitoring a vascular access during an extracorporeal blood treatment, comprising the steps of:
    flowing blood taken from a patient's vascular system through an arterial blood line of an extracorporeal blood circulation loop into a blood treatment machine;
    flowing blood out of the blood treatment machine back into the patient's vascular system through a venous blood line of the extracorporeal blood circulation loop thus forming a conductor loop that includes the patient's vascular system;
    inducing an electric current flow in a connection of the extracorporeal blood circulation loop with the patient's vascular system;
    measuring a current flowing in the conductor loop; and
    determining the vascular access is defective when a characteristic change in the electric current is detected.

2. The method according to claim 1, further comprising the steps of:
    disposing a field coil at a first location in the extracorporeal blood circulation loop;
    flowing an alternating current through the field coil;
    disposing an induction coil at a second location in the extracorporeal blood circulation loop, the second location being different from the first location; and
    monitoring a current induced in the induction coil to detect the disconnected vascular access.

3. The method according to claim 2, wherein the first location in the extracorporeal blood circulation is in one of the arterial and venous blood line, and the second location in the extracorporeal blood circulation is in another of the venous and arterial blood line.

4. The method according to claim 1, further comprising triggering an alarm when the disconnected vascular access is detected.

5. The method according to claim 1, further comprising interrupting the blood flow in the extracorporeal circulation loop when the disconnected vascular access is detected.

6. A device for extracorporeal blood treatment with an extracorporeal circulation loop, having a blood treatment machine, an arterial blood line connectable at one end to a patient's vascular system and at another end to an inlet of the blood treatment machine, and a venous blood line connectable at one end to an outlet of the blood treatment machine and at the other end to the vascular system of the patient, and a device for monitoring vascular access, the device for monitoring vascular access comprising:
    means for inducing an electric current flow in a connection of the extracorporeal circulation loop with the patient's vascular system, said means being disposed at a first location;
    means for measuring the induced electric current, disposed at a second location in the extracorporeal circulation loop, said second location being different from the first location; and
    an analyzer unit to determine if the vascular access is defective by monitoring a characteristic change in the induced electric current,
    wherein the blood treatment machine, the arterial blood line, the venous blood line and the patient's vascular system form a closed conductor loop.

7. The device according to claim 6, further comprising an alternating voltage generator connected to a field coil arranged at the first location, and an induction coil disposed at the second location.

8. The device according to claim 7, wherein the analyzer unit has a comparator to compare a voltage induced in the induction coil to a predetermined threshold value, and is adapted to detect the defective vascular access when the induced voltage is lower than the threshold value.

9. The device according to claim 6, wherein the means for inducing a current and the means for measuring the induced current are arranged respectively on the arterial blood line and on the venous blood line.

10. The device according to claim 6, further comprising an alarm generator for triggering an alarm when the disconnected vascular access is detected.

11. The device according to claim 6, further comprising means for interrupting the blood flow in the extracorporeal circulation loop when the disconnected vascular access is detected.

\* \* \* \* \*